(12) United States Patent
Reid et al.

(10) Patent No.: US 7,066,645 B2
(45) Date of Patent: Jun. 27, 2006

(54) POSITIONING DEVICE FOR USE IN RADIOGRAPHY

(75) Inventors: Paul Reid, Chessington (GB); Ian Luscombe, London (GB)

(73) Assignee: X-Ray Slider, Ltd. (GB)

( * ) Notice: Subject to any disclaimer, the term of this patent is extended or adjusted under 35 U.S.C. 154(b) by 0 days.

(21) Appl. No.: 10/508,722

(22) PCT Filed: Mar. 19, 2003

(86) PCT No.: PCT/GB03/01160

§ 371 (c)(1),
(2), (4) Date: May 9, 2005

(87) PCT Pub. No.: WO03/081335

PCT Pub. Date: Oct. 2, 2003

(65) Prior Publication Data
US 2005/0226388 A1    Oct. 13, 2005

(30) Foreign Application Priority Data
Mar. 20, 2002 (GB) .................. 0206634.8

(51) Int. Cl.
*G03B 42/02* (2006.01)
(52) U.S. Cl. ............... 378/167; 378/177; 378/181; 378/182
(58) Field of Classification Search ........ 378/167–188, 378/204–210; 229/68.2; 414/789.5; 5/659, 5/601, 612; D12/128, 133; 396/30
See application file for complete search history.

(56) References Cited

U.S. PATENT DOCUMENTS 2,447,468 A * 8/1948 Reyniers .................. 396/528
4,247,778 A    1/1981 Waerve
5,133,000 A    7/1992 Moller
5,226,068 A    7/1993 Strawder
5,239,716 A    8/1993 Fisk (Continued)

OTHER PUBLICATIONS

Lars Broen, A Bag for a Medical Item such as an X-Ray Cassette, Oct. 23, 2003, WIPO, Wo 03/087933 A1, entire document.*

*Primary Examiner*—Allen C. Ho
*Assistant Examiner*—John Corbett
(74) *Attorney, Agent, or Firm*—Thomas, Kayden, Horstemeyer & Risley LLP; Todd Deveau

(57) ABSTRACT

An X-ray cassette or a radiographic grid and X-ray cassette is (are) mounted within a device for positioning the cassette or grid and cassette beneath a patient lying upon a bed or other support to enable an X-ray image of a portion of the patient to be taken. The device has a plastics envelope formed of a material that is both substantially radiotranslucent and impervious to water or other biological fluids. This envelope defines first and second envelope sections separated from each other by a common edge. The first envelope section is generally rectangular in configuration and defines an openable pouch in which the X-ray cassette or radiographic grid and X-ray cassette are received. The second envelope section has a stiffening member therein. The second envelope section has its greatest width along the common edge and narrows to a minimum width at its edge furthest from the common edge. The stiffening member within the second envelope section is generally wedge shape in section, whereby the second envelope section has a thickness that tapers from a maximum thickness approximating the thickness of the radiographic grid and X-ray cassette at its greatest width adjacent the common edge to a minimum thickness at the furthest edge.

11 Claims, 2 Drawing Sheets

U.S. PATENT DOCUMENTS

| | | | |
|---|---|---|---|
| 5,377,254 A | * 12/1994 | Walling | 378/167 |
| 5,466,561 A | * 11/1995 | Rantanen | 430/347 |
| 5,473,664 A | 12/1995 | Strawder | |
| 5,703,925 A | 12/1997 | Wright | |
| 6,163,902 A | 12/2000 | Mollette et al. | |

* cited by examiner

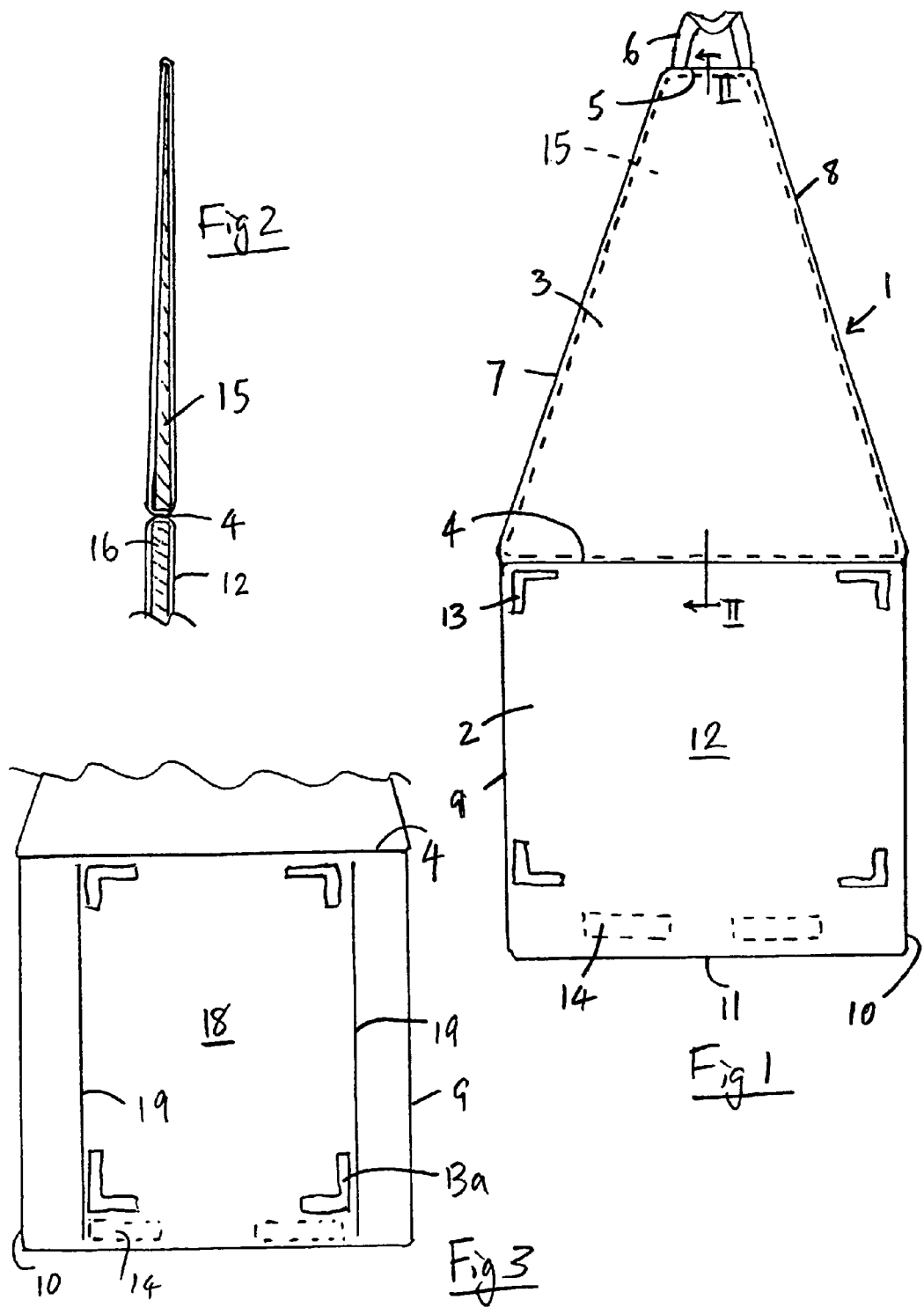

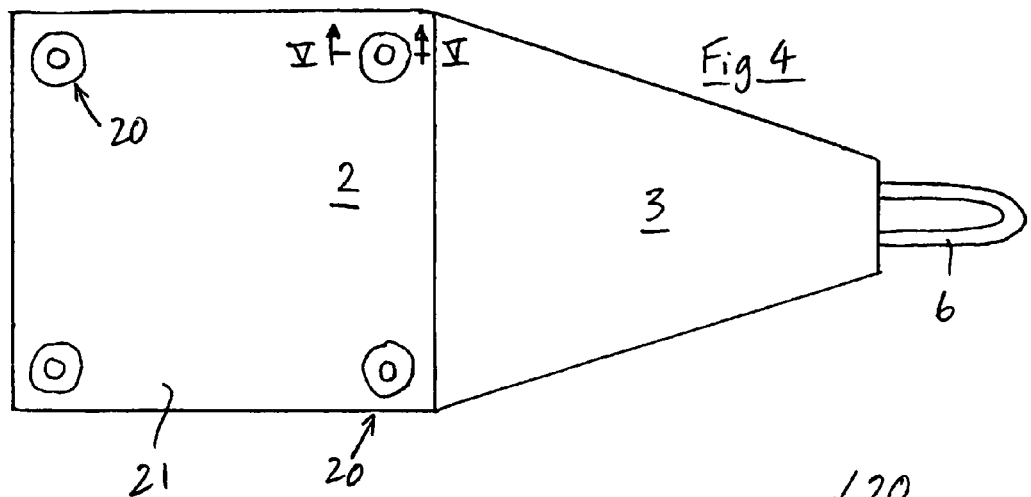
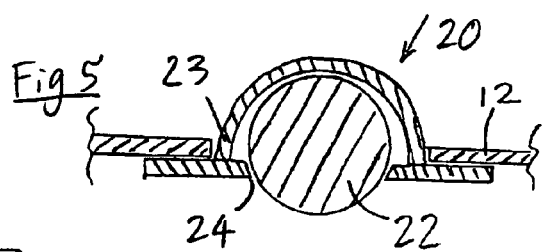
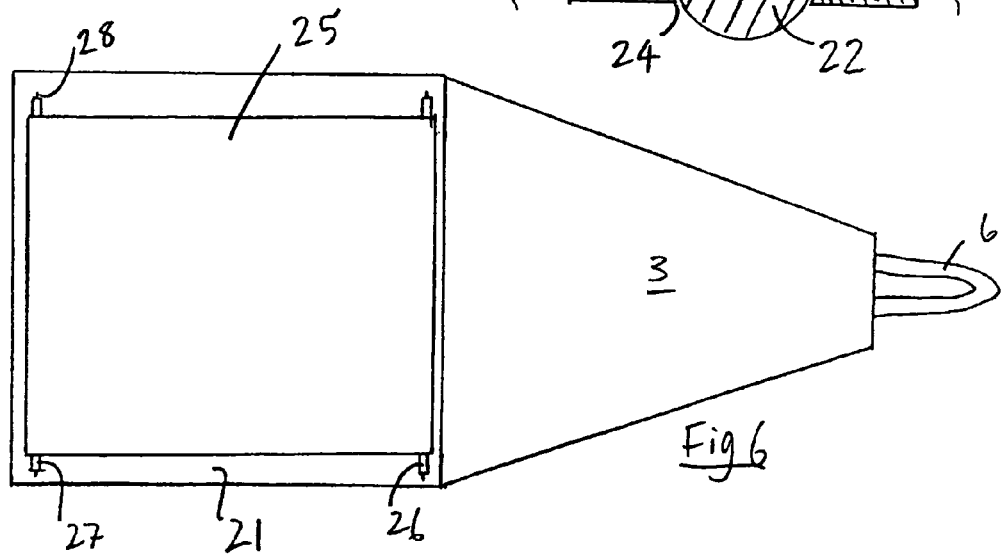
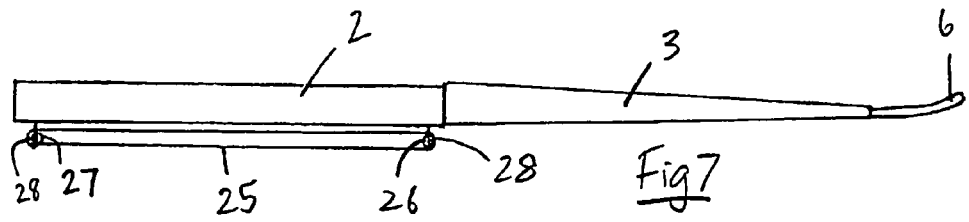

POSITIONING DEVICE FOR USE IN RADIOGRAPHY

RELATED APPLICATION

This application claims priority to and the benefit of GB 0206634.8 filed Mar. 20, 2002.

BACKGROUND OF THE INVENTION

This invention relates to radiography and to problems encountered in positioning a patient in relation to X-ray equipment and in relation to photographic film or digital media adapted for taking an X-ray picture of a portion of the patient.

Patients that are severely ill or are suffering from spinal or pelvic injury are often presented to a radiographer lying upon a bed or other support. In order that an X-ray image may be taken, the photographic film or digital medium, conventionally mounted in an X-ray cassette (together with a radiographic grid when the chest, spine or pelvis are to be imaged) must be positioned beneath the patient so that the patient can be placed beneath a source of X-rays to enable an X-ray image to be taken through a portion of their body.

Specially adapted beds or supports have previously been provided with a hollowed out section into which the radiographic grid and X-ray cassette may be inserted while the patient is lying upon the support. However, this is not satisfactory in use since the patient must first be transferred to the special support on which he will not be adequately supported at least at the time that the grid and cassette are being inserted from the side beneath him. Attempts to simply insert the grid and cassette, either alone or within a pouch, from the side and beneath the patient between an upper and a lower sheet on a conventional bed or support have also not proved satisfactory, firstly because of the friction encountered and secondly because of the jarring effect of the edge of the grid and cassette on the patient's spine or pelvis. X-ray cassettes for taking a chest or pelvic X-ray image and associated radiographic grids are quite substantial. The resultant image has dimensions of the order of 35 cm×43 cm, the orientation depending upon whether the image is taken in landscape or portrait format. The grid and cassette are slightly larger but known to radiographers as a "35×43" grid and cassette. The grid and cassette have a thickness of around 25 mm.

The patent literature includes a number of proposals for mounting X-ray cassettes from or within supports slid into position beneath a patient, but none is ideal. Thus: Wright in U.S. Pat. No. 5,703,925 proposes a support for an X-ray cassette that in use is positioned between a raised patient support platform and smooth flush surface below the patient support platform. A spade supports an x-ray cassette and is enabled to slid on this flush surface. Strawder (U.S. Pat. No. 5,226,068) employs a support to mount an X-ray cassette in a vertical position alongside a patient. The support is generally flat apart from a cavity enabling the cassette to stand upright on edge from the support and a ramp edge enabling the support to be more easily slid under a patient. Möller proposes a lifting device in U.S. Pat. No. 5,133,000 to raise a bed to slide an X-ray cassette beneath it. Waerve (U.S. Pat. No. 4,247,778) has a generally flat X-ray cassette chamber with a rounded leading edge to ease its insertion beneath a patient. An X-ray cassette can be moved within the chamber to enable an X-ray to be taken vertically through the patient in one configuration or horizontally through the patient in another configuration.

SUMMARY OF THE INVENTION

The device of the present invention has been devised with a view to overcoming the problems described above and to enable a radiographic grid and X-ray cassette to be more readily properly positioned beneath the appropriate portion of a patient already lying on a bed or other support with a minimum of jarring or movement to the spine or pelvis when inserting the grid and X-ray cassette beneath the patient.

In accordance with a first aspect of the present invention, there is provided a positioning device for use in radiography to position an X-ray cassette or a radiographic grid and X-ray cassette beneath a patient lying upon a bed or other support to enable an X-ray image of a portion of the patient to be taken; the device comprising: a plastics envelope formed of a material that is both substantially radiotranslucent and impervious to water or other biological fluids; the envelope defining first and second envelope sections separated from each other by a common edge; the first envelope section being generally rectangular in configuration and defining an openable pouch dimensioned to receive an X-ray cassette or radiographic grid and X-ray cassette therein; and the second envelope section having a stiffening member therein, the second envelope section having its greatest width along said common edge and narrowing to a minimum width at its edge furthest from said common edge, and the stiffening member within the second envelope section being generally wedge shape in section, whereby the second envelope section tapers from a maximum thickness approximating the thickness of a radiographic grid and X-ray cassette at its greatest width adjacent the common edge to a minimum thickness at said furthest edge.

The furthest edge where the second envelope section with its stiffening member therein has both its minimum thickness and narrowest width is suitably provided with a handle formed of tape. By separating a top sheet from its under sheet on the bed or support on which the patient is lying and inserting the thin and narrow edge between the two sheets, the second envelope section may readily be slid beneath the patient until the handle may be grabbed from the far side. From that point on, the device may be pulled. Forming the envelope of the device from plastics reduces friction with the sheets. In the preferred arrangement, the plastics envelope is provided with a low-friction varnish coating. As a result of the wedge shape of the stiffening member, the patient is gradually and almost imperceptibly raised as the second envelope section is inserted beneath them and receives no sudden jolt as the grid and cassette, inserted into the pouch, then pass beneath them, because the thickness of the stiffening member adjacent the common edge approximates the thickness of the grid and cassette within the pouch on the other side of the common edge.

After exposure to X-rays, the cassette or grid and cassette may be removed from beneath the patient just as easily as they were inserted.

The X-ray image may need to be taken either in landscape or in portrait format. To readily enable this, the first envelope section is preferably formed so as to define two pouches alongside each other with a common wall extending therebetween, one said pouch being dimensioned so as to accept the grid and cassette in landscape position and the other pouch being dimensioned to allow insertion of the grid and cassette in portrait position.

It will be appreciated that with this configuration, the landscape pouch or the portrait pouch will be uppermost depending upon which side of the device is uppermost. The respective landscape and portrait pouches may be identified on the outer surface of the envelope on its two sides by generally "L-shaped" markings (lead-free to maintain radiotranslucency) identifying the corners of the cassette when inserted into the corresponding pouch. This readily enables a radiographer to choose which way up he wishes to use the device and insert the cassette or grid and cassette into the appropriate pouch. The pouches may suitably be closed by hook-and-loop fastenings, such as those sold under the VELCRO® Trademark.

In a second and alternative aspect of this invention, there is provided a radiographic grid and X-ray cassette mounted within a device for positioning the grid and cassette beneath a patient lying upon a bed or other support to enable an X-ray image of a portion of the patient to be taken; the device comprising: a plastics envelope formed of a material that is both substantially radiotranslucent and impervious to water or other biological fluids; the envelope defining first and second envelope sections separated from each other by a common edge; the first envelope section being generally rectangular in configuration and defining an openable pouch in which the radiographic grid and X-ray cassette are received; and the second envelope section having a stiffening member therein, the second envelope section having its greatest width along said common edge and narrowing to a minimum width at its edge furthest from said common edge, and the stiffening member within the second envelope section being generally wedge shape in section, whereby the second envelope section has a thickness that tapers from a maximum thickness approximating the thickness of the radiographic grid and X-ray cassette at its greatest width adjacent the common edge to a minimum thickness at said furthest edge.

BRIEF DESCRIPTION OF THE DRAWINGS

The invention is hereinafter more particularly described by way of example only with reference to the accompanying drawings, in which:

FIG. 1 is a plan view of an embodiment of positioning device in accordance with this invention;

FIG. 2 is a partial sectional view taken along the lines II—II in FIG. 1;

FIG. 3 shows part of the reverse plan view for an alternative and preferred embodiment of the device;

FIG. 4 is an underneath plan view of another embodiment of the device;

FIG. 5 is an enlarged sectional view taken along the line V—V in FIG. 4;

FIG. 6 is an underneath plan view of yet another embodiment of the device; and

FIG. 7 is a side elevational view of the embodiment of FIG. 6.

DESCRIPTION OF PREFERRED EMBODIMENTS

As can best be seen from FIG. 1, a positioning device according to the present invention for use in radiography to position an X-ray cassette or a radiographic grid and X-ray cassette beneath a patient lying upon a bed or other support to enable an X-ray image of a portion of the patient to be taken essentially comprises a plastics envelope 1 defining first and second envelope sections 2,3 separated from each other by a common edge 4. As can be seen from FIG. 1, the first envelope section 2 is generally rectangular in configuration while the second envelope section 3 has the shape of a trapezium or truncated triangle the width of which narrows from edge 4 to a minimum width at its furthest edge 5, where a handle 6 formed of cotton or other fabric tape is attached. Although the edges of envelope section 3 are shown as straight lines, they could be curved. The envelope sections are sealed from each other along the common edge 4 and also sealed along their remaining edges 5, 7, 8, 9 and 10, leaving only edge 11 of section 2 open, in effect defining a pouch.

The pouch is dimensioned to receive a conventional X-ray cassette alone or a radiographic grid and X-ray cassette, for example a "35×43" grid and cassette designed to take chest or pelvic X-ray images with a dimension of the order of 35 cm×43 cm. Outside surface 12 of section 2 has lead-free L-shaped corner position markers 13 thereon indicating the position of such a cassette or grid and cassette when fully inserted into the pouch. The pouch is releasably closed by means of co-operating hook-and-loop fastening strips 14 adhered to the inside surfaces of the plastics envelope 1.

Sealed within envelope section 3 is a stiffening member 15 which is generally wedge-shaped in section, as shown in FIG. 2 having its greatest thickness adjacent the common edge 4 and its narrowest thickness adjacent the furthest edge 5. Stiffening member 15 may be provided as a fully rigid board but preferably has some flexibility to aid in inserting the device, leading with edge 5, beneath a patient lying upon a bed or other support, for example by separating a top sheet from its under sheet and sliding the device between the two sheets. If the stiffening member 15 has some flexibility, this will be greatest adjacent edge 5 where it is at its thinnest and least adjacent edge 4. As the device is pushed beneath the patient, the patient will feel very little but is slowly raised by the thickness of section 3 with its stiffening member 15 therewithin until the patient is raised sufficiently by the time edge 4 passes underneath the patient for the grid and cassette 16 within envelope section 2, having a thickness (generally of 25 mm when both grid and cassette are used) approximating the greatest thickness of stiffening member 15, to pass beneath the patient without significantly jarring or jolting their pelvis or spine.

As will be apparent from the positions of L-shaped corner indications 13, the pouch defined by envelope section 2 is designed to receive grid and cassette 16 with the longer of their edges parallel to and adjacent the common edge 4. Depending upon the purpose for which an X-ray image is to be taken, it may be desirable to take that image either in portrait or landscape format. To allow for this, in an alternative and preferred embodiment, as illustrated by FIG. 3, envelope section 2 suitably provides two separate pouches alongside each other by having an internal medial wall 17 attached internally of envelope section 2 to the wall 18 opposite wall 12, at least along edges 19. As will be seen from the corresponding corner markings 13a on wall 18, the second pouch so defined within envelope section 2 allows the grid and cassette to be inserted only in the opposite configuration with their shorter edge adjacent common edge 4.

Plastics material for envelope 1 must necessarily be substantially radiotranslucent (transparent to X-rays) and should also be impervious to water and other biological fluids such as blood and urine. The surface of the envelope can be readily cleaned to meet the hygiene standards required in hospitals. A suitable material is heavyweight polyvinylchloride. Preferably this material is given a low-friction varnish coating to enable the device to slip easily between two sheets on a bed. Coated PVC of this kind is available from Lows Ltd of Dundee. A suitable material for the stiffening member is a PVC plastics foam, but other cardboard or plastics members could be used, if formed with the appropriate profile.

All the edges of the envelope sections that are required to be sealed are suitably plastics welded under conditions of heat and pressure sufficient to soften and join the edges of the plastics sheets concerned.

The material employed for the envelope and/or a low-friction coating applied to should alone be sufficient to enable the device to be slid beneath a patient. However, this ability to insert the device beneath a patient can be enhanced as explained below.

As shown in FIGS. 4 and 5, a number of roller ball units 20, here four, one at each corner, are mounted on the bottom surface 21 of the first envelope section 2. Each roller ball unit 20 comprises a ball 22 freely rotatable within a cage 23, the opening 24 of which is smaller than the diametric cross-section of the ball. The balls rotate as the device is pulled beneath a patient. The balls may be of steel, but are preferably of Nylon (for example Nylon 11), which is effectively self-lubricating.

In a variation, not illustrated, the rollers are replaced by small wheels, for example castors, or rollers.

In the alternative arrangement illustrated in FIGS. 6 and 7, an endless track 25 is mounted beneath the device, the track passing around pulleys, here rollers 26, 27 suitably made of steel or Nylon, as the device is pulled beneath a patient. The rollers are rotatable on axles 28 supported from the underside 21 of the first envelope section 2. Track 25 is suitably formed as an endless belt or as a length of belting joined at its ends, in either case being of a material with a relatively high co-efficient of friction (for example: rubber) to impart a generally non-slip surface to the track.

In a variation, not illustrated, rather than a single track 24 across the greater part of the width of the underside 21 of envelope section 2, separate tracks may be provided adjacent the marginal side edges of underside 21, rather in the manner of tank tracks, and further pulleys may be mounted intermediate the end pulleys to aid in support of the track at such intermediate positions.

As will be appreciated, any arrangement with auxiliary travel means such as roller balls, wheels, rollers or tracks must necessarily be thicker than would be the case for a corresponding device without such auxiliary travel means. The greater the thickness, the more the patient is moved on insertion of an X-ray cassette beneath them. Accordingly, arrangements without auxiliary travel means will usually be preferred except where the patient is unusually heavy or the surface on which they are lying is not even, and may not be a bed. Devices in accordance with the embodiments of FIGS. 4 to 7 are particularly useful in veterinary practice, where—for example—an animal may need to be X-rayed while lying on the floor.

The invention claimed is:

1. A positioning device for use in radiography to position an X-ray cassette or a radiographic grid and X-ray cassette beneath a patient lying upon a bed or other support to enable an X-ray image of a portion of the patient to be taken; the device comprising:
    a plastics envelope formed of a material that is both substantially radiotranslucent and impervious to water or other biological fluids;
    the envelope defining first and second envelope sections separated from each other by a common edge;
    the first envelope section being generally rectangular in configuration and defining an openable pouch dimensioned to receive an X-ray cassette or radiographic grid and X-ray cassette therein; and
    the second envelope section having a stiffening member therein,
        the second envelope section having its greatest width along said common edge and narrowing to a minimum width at its edge furthest from said common edge, and
        the stiffening member within the second envelope section being generally wedge shape in section, whereby the second envelope section has a thickness that tapers from a maximum thickness approximating the thickness of a radiographic grid and X-ray cassette at its greatest width adjacent the common edge to a minimum thickness at said furthest edge.

2. A device according to claim 1, wherein the said furthest edge is provided with a handle formed of tape, the handle being graspable from the opposite side of a bed or support when the said furthest edge is slid beneath a patient from one side of the said bed or support, thereafter enabling the device with an X-ray cassette or a radiographic grid and X-ray cassette within the said pouch to be pulled into position beneath the patient.

3. A device according to claim 1, wherein the outer surface of the first envelope section is provided with lead-free markings, identifying the position of an X-ray cassette or radiographic grid and X-ray cassette fully inserted into said pouch to aid in correct positioning.

4. A device according to claim 1, wherein the first envelope section defines two pouches therein, one in landscape orientation and the other in portrait orientation for the X-ray image.

5. A device according to claim 4, wherein space within the first envelope section is divided by a substantially medial wall to provide two pouches alongside each other, one associated with each side of the device.

6. A device according to claim 5, wherein the opposite outer surfaces of the first envelope section are each provided with lead-free markings, identifying the position of an X-ray cassette or radiographic grid and X-ray cassette when fully inserted into the immediately underlying pouch, so that one side of the device has markings indicating its use for landscape images, and the other side of the device has markings indicating its use for portrait images.

7. A device according to claim 1, wherein the stiffening member is at least partially flexible rather than being essentially rigid, its resistance to flexure increasing from said furthest edge towards said common edge.

8. A device according to claim 1, wherein the underside of the first envelope section is provided with auxiliary travel means adapted to assist in location of the first envelope section beneath a patient.

9. A device according to claim 8, wherein the auxiliary travel means comprise a plurality of roller balls.

10. A device according to claim 8, wherein the auxiliary travel means comprise at least one endless track constrained to pass around pulleys.

11. A radiographic grid and X-ray cassette mounted within a device for positioning the grid and cassette beneath a patient lying upon a bed or other support to enable an X-ray image of a portion of the patient to be taken; the device comprising:
    a plastics envelope formed of a material that is both substantially radiotranslucent and impervious to water or other biological fluids;
    the envelope defining first and second envelope sections separated from each other by a common edge;

the first envelope section being generally rectangular in configuration and defining an openable pouch in which the radiographic grid and X-ray cassette are received; and the second envelope section having a stiffening member therein, the second envelope section having its greatest width along said common edge and narrowing to a minimum width at its edge furthest from said common edge, and the stiffening member within the second envelope section being generally wedge shape in section, whereby the second envelope section has a thickness that tapers from a maximum thickness approximating the thickness of the radiographic grid and X-ray cassette at its greatest width adjacent the common edge to a minimum thickness at said furthest edge.

* * * * *